(12) United States Patent
Stahmann et al.

(10) Patent No.: US 10,029,104 B2
(45) Date of Patent: Jul. 24, 2018

(54) LEADLESS PACEMAKER WITH END-OF-LIFE PROTECTION

(71) Applicant: Cardiac Pacemakers, Inc., St. Paul, MN (US)

(72) Inventors: Jeffrey E. Stahmann, Ramsey, MN (US); Benjamin J. Haasl, Forest Lake, MN (US); Keith R. Maile, New Brigthon, MN (US); William J. Linder, Golden Valley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 145 days.

(21) Appl. No.: 14/577,722

(22) Filed: Dec. 19, 2014

(65) Prior Publication Data
US 2015/0174412 A1 Jun. 25, 2015

Related U.S. Application Data

(60) Provisional application No. 61/919,575, filed on Dec. 20, 2013, provisional application No. 61/919,572, filed on Dec. 20, 213, provisional application No. 61/919,567, filed on Dec. 20, 2013.

(51) Int. Cl.
*A61N 1/37* (2006.01)
*A61N 1/375* (2006.01)
*A61N 1/372* (2006.01)
*A61N 1/39* (2006.01)

(52) U.S. Cl.
CPC ......... *A61N 1/3708* (2013.01); *A61N 1/3756* (2013.01); *A61N 1/37223* (2013.01); *A61N 1/37235* (2013.01); *A61N 1/3962* (2013.01)

(58) Field of Classification Search
CPC .................................................. A61N 1/3708
See application file for complete search history.

(56) References Cited

U.S. PATENT DOCUMENTS 5,331,966 A 7/1994 Bennett et al.
5,496,353 A 3/1996 Grandjean et al.
(Continued)

FOREIGN PATENT DOCUMENTS

CN 1307495 A 8/2001
CN 1985751 A 6/2007
(Continued)

OTHER PUBLICATIONS

International Preliminary Report on Patentability issued in PCT/US2014/071714, dated Jun. 30, 2016, 11 pages.
(Continued)

*Primary Examiner* — Carl H Layno
*Assistant Examiner* — Jennifer Ghand
(74) *Attorney, Agent, or Firm* — Faegre Baker Daniels LLP

(57) ABSTRACT

An implantable medical device includes operational circuitry, such as a therapy circuit. The implantable medical device also includes a power source configured to deliver energy to the operational circuitry, and a deactivation element configured to disable the therapy circuit. A power manager is configured to detect an end-of-life condition of the power source and, in response to detecting the end-of-life condition, cause the deactivation element to reversibly disable the therapy circuit.

17 Claims, 11 Drawing Sheets

(56) References Cited

U.S. PATENT DOCUMENTS

| | | | |
|---|---|---|---|
| 5,792,202 A * | 8/1998 | Rueter | A61N 1/37247 607/27 |
| 5,876,423 A | 3/1999 | Braun | |
| 6,016,448 A | 1/2000 | Busacker et al. | |
| 6,400,988 B1 * | 6/2002 | Gurewitsch | A61N 1/3708 607/29 |
| 7,634,313 B1 | 12/2009 | Kroll et al. | |
| 7,650,186 B2 | 1/2010 | Hastings et al. | |
| 7,694,809 B2 | 4/2010 | Garbini et al. | |
| 7,991,467 B2 | 8/2011 | Markowitz et al. | |
| 8,214,164 B2 | 7/2012 | Gandhi et al. | |
| 8,386,051 B2 | 2/2013 | Rys | |
| 8,478,408 B2 | 7/2013 | Hastings et al. | |
| 2003/0050676 A1 | 3/2003 | Hubelbank et al. | |
| 2007/0179547 A1 | 8/2007 | Armstrong et al. | |
| 2008/0300660 A1 * | 12/2008 | John | A61N 1/3785 607/61 |
| 2009/0204170 A1 | 8/2009 | Hastings et al. | |
| 2009/0292341 A1 * | 11/2009 | Parramon | A61N 1/3605 607/61 |
| 2009/0312809 A1 | 12/2009 | Gandhi et al. | |
| 2011/0213434 A1 * | 9/2011 | Signoff | A61N 1/378 607/8 |
| 2012/0172941 A1 * | 7/2012 | Rys | A61N 1/025 607/5 |
| 2012/0197332 A1 | 8/2012 | Peichel et al. | |
| 2012/0265266 A1 * | 10/2012 | Colborn | A61N 1/36053 607/45 |
| 2013/0253343 A1 | 9/2013 | Waldhauser et al. | |
| 2014/0277277 A1 * | 9/2014 | Gordon | A61N 1/378 607/59 |
| 2015/0174413 A1 | 6/2015 | Stahmann et al. | |
| 2015/0174414 A1 | 6/2015 | Stahmann et al. | |

FOREIGN PATENT DOCUMENTS

| | | |
|---|---|---|
| CN | 101516442 A | 8/2009 |
| WO | 2014182680 A1 | 11/2014 |
| WO | 2015095818 A1 | 6/2015 |

OTHER PUBLICATIONS

International Search Report and Written Opinion issued in PCT/US2014/071714, dated May 6, 2015, 15 pages.

* cited by examiner

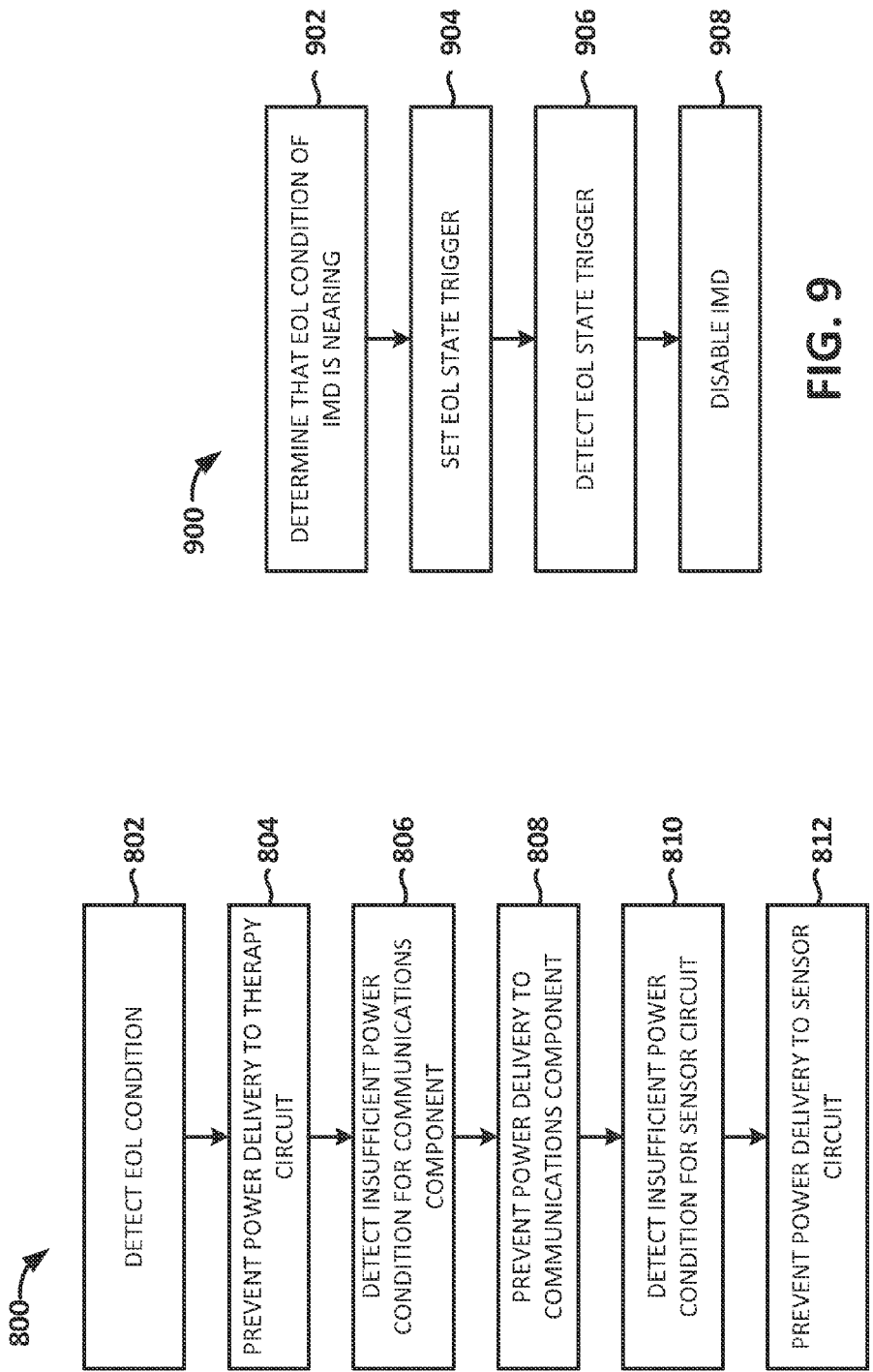

LEADLESS PACEMAKER WITH END-OF-LIFE PROTECTION

CROSS-REFERENCE TO RELATED APPLICATION

This application claims priority to Provisional Application Nos. 61/919,572; 61/919,575; and 61/919,567, all of which were filed on Dec. 20, 2013, and each of which is herein incorporated by reference in its entirety.

TECHNICAL FIELD

The present invention relates to an implantable system having an implantable medical device. More specifically, the invention relates to managing and end-of-life condition associated with an implantable medical device.

BACKGROUND

Implantable medical devices include, among other things, cardiac rhythm management (CRM) devices such as pacers, cardioverters, defibrillators, cardiac resynchronization therapy (CRT) devices, leadless pacing seeds, as well as combination devices that provide more than one of these therapy modalities to a subject. Such implantable devices are typically powered by a battery. As the battery's useful life becomes exhausted, the implanted device may malfunction, causing errors in the therapy it provides and/or its communication with other devices.

SUMMARY

In Example 1, the present disclosure describes an implantable medical device comprising operational circuitry, wherein the operational circuitry comprises at least one of a therapy circuit and a sensor circuit. The implantable medical device also includes a communications module, a power source configured to deliver energy to the operational circuitry, and a deactivation element configured to at least partially disable the operational circuitry by interrupting delivery of energy from the power source to the operational circuitry. A power manager disposed within the specification is configured to detect an end-of-life condition of the power source and, in response to detecting the end-of-life condition, cause the deactivation element to at least partially reversibly disable the operational circuitry.

In Example 2, the implantable medical device of Example 1, wherein the implantable medical device comprises a leadless cardiac pacing seed.

In Example 3, the implantable medical device of Example 1, wherein the operational circuitry comprises the therapy circuit.

In Example 4, the implantable medical device of Example 3, wherein the deactivation element is configured to prevent energy from being delivered to the therapy circuit.

In Example 5, the implantable medical device of Example 1, further comprising a memory component configured to store an indication of a post end-of-life state of the implantable medical device.

In Example 6, the implantable medical device of Example 5, wherein the memory component comprises an active storage element.

In Example 7, the implantable medical device of Example 6, wherein the power manager is configured to allow energy to be delivered to the memory component during the end-of-life state.

In Example 8, the implantable medical device of Example 5, wherein the memory component comprises a non-volatile memory element.

In Example 9, the implantable medical device of Example 9, wherein the memory component is further configured to store a plurality of operational parameters during the end-of-life state.

In Example 10, the implantable medical device of Example 10, wherein the power source comprises a rechargeable battery.

In Example 11, the implantable medical device of Example 11, further comprising a controller, wherein the controller is configured to access the plurality of operational parameters in response to receiving an activation signal.

In Example 12, the implantable medical device of Example 11, wherein the controller is configured to restore the device to its pre-end-of-life state using the operational parameters.

In Example 13, the present disclosure describes a leadless cardiac pacing seed comprising a therapy circuit, a communications module, and a power source configured to deliver energy to the therapy circuit and the communications module. The leadless cardiac pacing seed also includes a deactivation element configured to disable at least one of the therapy circuit and the communications module by reversibly interrupting delivery of energy from the power source to the therapy circuit or the communications module. A power manager disposed within the leadless cardiac pacing seed is configured to detect an end-of-life condition of the seed and, in response to detecting the end-of-life condition, cause the deactivation element to reversibly disable at least one of the therapy circuit and the communications module.

In Example 14, the leadless cardiac pacing seed of Example 13, further comprising a memory component configured to store an indication of an end-of-life state.

In Example 15, the leadless cardiac pacing seed of Example 14, wherein the memory component comprises an active storage element.

In Example 16, the leadless cardiac pacing seed of Example 15, wherein the power manager is configured to allow energy to be delivered to the memory component during the end-of-life state.

In Example 17, the leadless cardiac pacing seed of Example 14, wherein the memory component comprises a non-volatile memory element.

In Example 18, the leadless cardiac pacing seed of Example 17, wherein the memory component is further configured to store a plurality of operational parameters during the end-of-life state, and wherein the controller is configured to access the plurality of operational parameters in response to receiving an activation signal.

In Example 19, the leadless cardiac pacing seed of Example 18, wherein the controller is configured to restore the device to its pre-end-of-life state using the operational parameters.

In Example 20, the present disclosure describes a cardiac pacing system comprising an implantable leadless cardiac pacing seed configured to deliver electrostimulation therapy to a patient and an external device. The implantable leadless cardiac pacing seed includes a therapy circuit, a communications module configured to receive a deactivation signal from the external device, and a power source configured to deliver energy to the therapy circuit and the communications module. A power manager is configured to detect an end-of-life condition of at least one of the power source and the therapy circuit and, in response to detecting the end-of-life condition, place the implantable leadless cardiac pacing seed in an end-of-life state. The implantable leadless cardiac pacing seed also includes a deactivation element configured to interrupt delivery of energy from the power source to the therapy circuit so as to reversibly disable the therapy circuit in response to the deactivation signal being received by the communications module. Additionally, the leadless cardiac pacing seed includes a memory component configured to store an indication of an end-of-life state of the seed.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 8 is a flow diagram depicting an illustrative method of deactivating an IMD, in accordance with embodiments of the invention;

FIG. 9 is another flow diagram depicting an illustrative method of deactivating an IMD, in accordance with embodiments of the invention;

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

DETAILED DESCRIPTION

Figure 1:
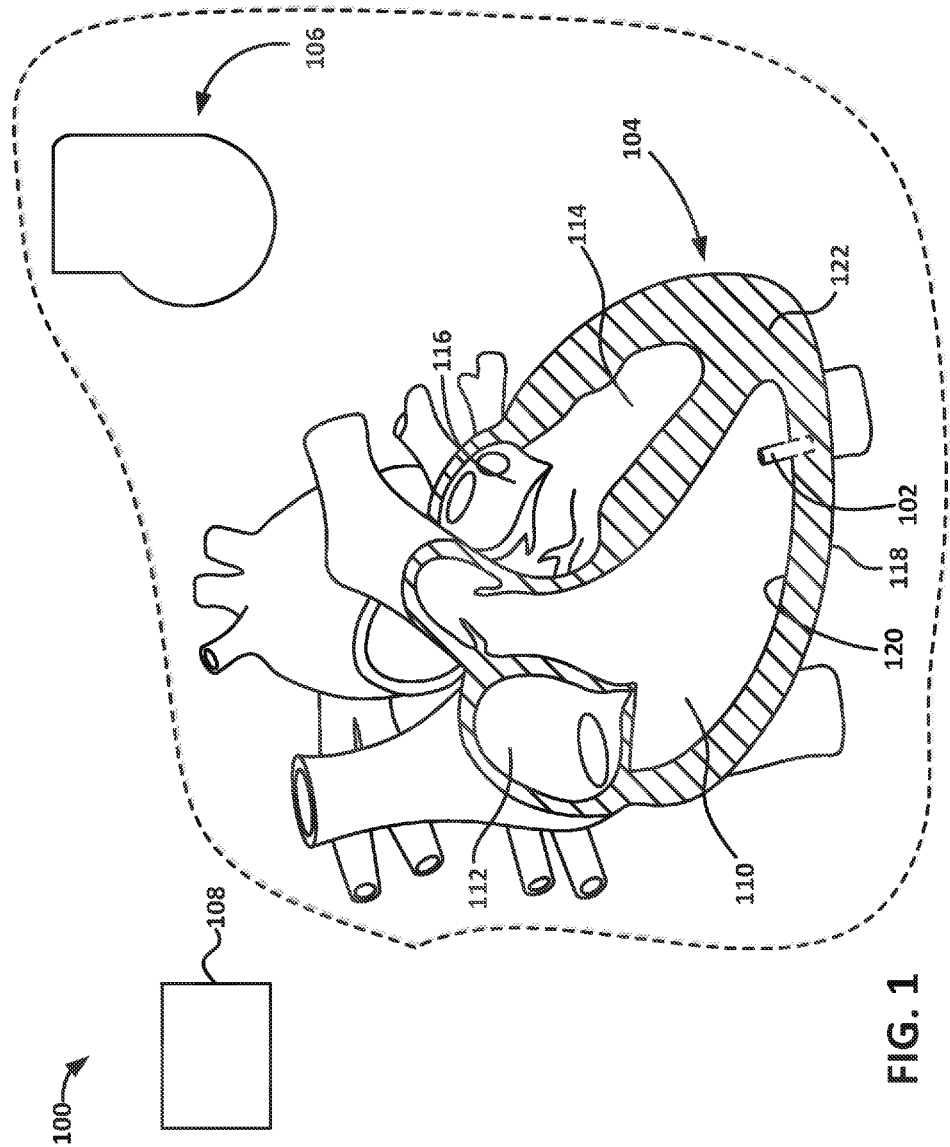
FIG. 1 is a schematic illustration of an implantable system having a leadless implantable stimulator and a control device in an implanted state, in accordance with embodiments of the invention.

FIG. 1 is a schematic illustration of an implantable system 100 including an implantable medical device (IMD) 102 implanted within a chamber of a patient's heart 104. In the embodiment illustrated in FIG. 1, the IMD 102 is a wireless electrode stimulator assembly, referred to herein, interchangeably, as a "seed." The system 100 also includes a co-implanted device 106 that is configured to communicate with the seed 102. In various embodiments, the co-implanted device 106 can be implanted subcutaneously within an implantation location or pocket in the patient's chest or abdomen. The co-implanted device 106 may be an implantable medical device known in the art or later developed, for delivering an electrical therapeutic stimulus to the patient. In various embodiments, the co-implanted device 106 may provide therapy and/or diagnostic data about the patient and/or the co-implanted device 106. In various embodiments, the co-implanted device 106 may be a communication repeater for extra-corporeal communication to external device 108. In various embodiments, the co-implanted device 106 may be a pacemaker, an implantable cardioverter defibrillator (ICD) device, or a cardiac resynchronization therapy (CRT) device. In various embodiments, the implantable control device 106 may include both defibrillation and pacing/CRT capabilities (e.g., a CRT-D device).

In embodiments, the co-implanted device 106 includes circuitry to sense and analyze the heart's electrical activity, and to determine if and when a pacing electrical pulse needs to be delivered and, in embodiments having multiple seeds 102, by which of the seeds 102 the pulse should be delivered. The sensing capability may be made possible by having sense electrodes included within the physical assembly of the co-implanted device 106. Alternatively, a conventional single or dual lead pacemaker (not shown in FIG. 1) may sense the local cardiac electrocardiogram (ECG) and transmit this information to the co-implanted device 106 for use in determination of the timing of seed firing. In embodiments, the seed 102 may include sensing capability, and may communicate sensed information to other seeds 102 and/or to the co-implanted device 106. In embodiments, the co-implanted device 106 may transmit charge energy and data, such as pace trigger signals, pacing amplitude information, and pulse width information to the seed 102 via radio-frequency (RF) communications, acoustic communications, inductive communications, electrical communications, microwave communications, conductive communications, and/or the like.

In the embodiment shown in FIG. 1, the seed 102 is implanted in the right ventricle 110. The seed 102 may sense electrical signals of the heart 104 and/or deliver electrical pulses to the heart 104 in an attempt to correct an arrhythmia and restore sinus rhythm. In other embodiments, the seed 102 may be implanted or placed within any chamber of the heart 104. For example, the seed 102 may be implanted in the right atrium 112, the left ventricle 114, or the left atrium 116. In addition, the seed 102 may be implanted into or be placed on the epicardium 118, for example the epicardium 118 of the right ventricle 110, the right atrium 112, the left ventricle 114 or the left atrium 116. In such cases, the seed 102 can be delivered through the circulatory system of the heart 104 to the location of interest, or it can be implanted or placed on the epicardium 118 by gaining access to the pericardial space. In some embodiments, the seed 102 may be implanted through the epicardium 118 or endocardium 120 and into the myocardium 122. In other embodiments, the system 100 may include a plurality of seeds 102, each placed in, implanted in, or attached to a different chamber or a different part of the heart 104.

In embodiments, implantable systems such as implantable system 100 may be unipolar, multipolar (e.g., bipolar, quadpolar, etc.) or configurable such that a unipolar or multipolar operation can be selected. In a unipolar system, an electrode of the seed 102 acts as one pole of an electrical system, and the second pole of the electrical system may be located remotely from the electrode. For example, the second pole of the electrical system may be located on the housing of the seed 102 or on a wire connected to the seed 102. Various other configurations for unipolar devices are known in the art.

In a bipolar system, the implantable system 100 may have two or more electrodes disposed near the site of treatment. For example, a seed 102 may have two electrodes disposed on the body of the seed 102 (e.g., a tip electrode and a ring electrode). The two electrodes may act as the two electrical poles of the seed 102. Various other configurations for bipolar electrodes are known in the art. According to embodiments, the electrodes of the seeds 102 also may be configured to sense certain physiological attributes of the heart 104. For example, the heart's 104 natural electrical signals can be received by an electrode and transmitted to a remote location (e.g., the co-implanted device 106). In addition, other sensing mechanisms that are known in the art may be placed within, on or near the seeds 102, and may include, for example, pressure sensors, motion sensors, and/or the like. Although the seed 102, and corresponding system 100, illustrated in FIG. 1 is configured for cardiac therapy, other implantable seed applications, such as those configured for neurostimulation, e.g., Spinal Cord Stimulation (SCS), Deep Brain Stimulation (DBS), and Functional Electrical Stimulation (FES), also are contemplated within the scope of various embodiments.

In embodiments, the seed 102 has an internal receiver that may receive communications and/or energy from co-implanted device 106, which may include a transmitter. The co-implanted device 106 may include a pulse generator that supplies an appropriate time-varying energy (e.g., current or voltage) to the seed 102. The seed 102 may include a power source for storing electrical energy, and may also have a triggering mechanism to deliver stored electrical energy to adjacent heart tissue.

Figure 2:
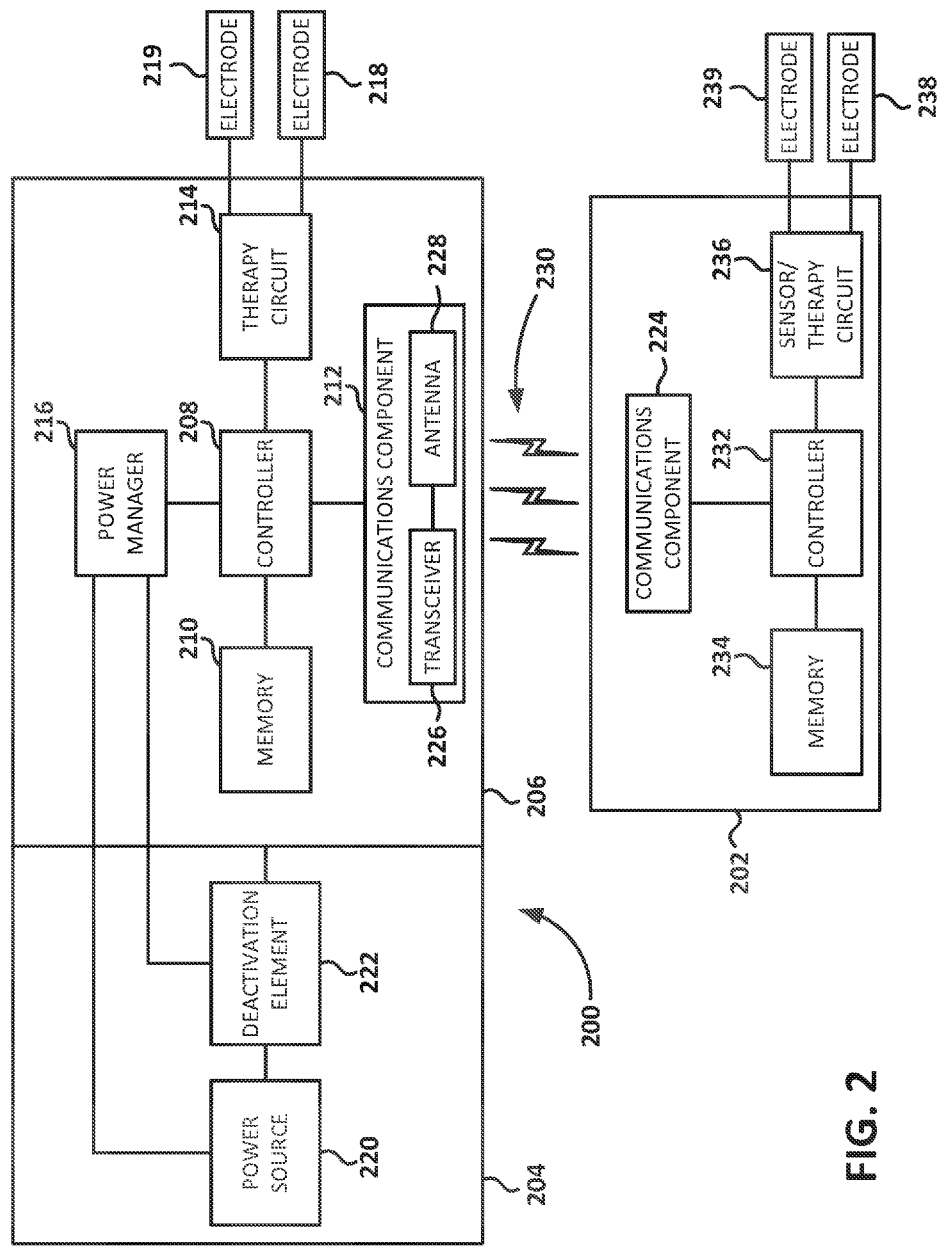
FIG. 2 is a schematic block diagram of an implantable system having an IMD and a control device, in accordance with embodiments of the invention.

FIG. 2 is a block schematic diagram of a system including an IMD 200 (such as, for example, the seed 102 depicted in FIG. 1) and a co-implanted device 202. As illustrated in FIG. 2, the IMD 200 includes a power component 204 that provides electrical energy to a set 206 of components. The set 206 of components include a controller 208, a memory 210, a communications component 212, a therapy circuit 214, and a power manager 216. As shown in FIG. 2, the therapy circuit 214 is coupled to electrodes 218 and 219 and is configured to provide stimulation energy to the electrodes, which, in turn, provides the energy to a patient's body (e.g., a location in a patient's heart). According to embodiments, the IMD 200 may include more than two electrodes. The power component 204 includes a power source 220 configured to store electrical energy and a deactivation element 222 configured to prevent, upon its activation, energy from being delivered to one or more components (e.g., the controller 208, the communications component 212, the therapy circuit 214) of the IMD 200. According to embodiments, the power source 220 may include one or more batteries, capacitors, and/or the like. In embodiments, the IMD 200 may include other components such as, for example, one or more sensor circuits (not shown), coupled to one or more sensors and/or the electrodes 218 and 219, for sensing physiological parameters.

According to embodiments, the power manager 216 may be configured to detect an end-of-life (EOL) condition associated with the IMD 200. In embodiments, the power manager 216 may detect an EOL condition by determining that the capacity of the power source has been depleted below a predetermined threshold (e.g., 10% of total capacity), that the operation of one or more components (e.g., the controller 208, the therapy circuit 214, and/or the communications component 212) appears to be altered due to a deficiency of energy being delivered from the power source 220, and/or the like. In embodiments, the power manager 216 may monitor the operation of various components of the IMD 200 by accessing data from the controller 208. In other embodiments, the power manager 216 may monitor the operation of components directly.

According to various embodiments, the deactivation element 222 may comprise one or more elements, circuits, logical components, and/or the like, and may be configured to prevent electrical energy from being delivered from the power source 220 or to one or more components of the IMD 200. In embodiments, for example, the deactivation element 222 may be, or include, a short-circuit element (e.g., a fuse), a switch (e.g., a field-effect-transistor (FET) fuse), a crowbar mechanism, and/or the like. The deactivation element 222 may be configured to selectively prevent electrical energy from being delivered to certain components of the IMD 200 and, in embodiments, the deactivation element 222 may be configured to prevent electrical energy from being delivered to all of the components of the IMD 200. The deactivation element 222 may, in embodiments, be configured to permanently and/or reversibly prevent electrical energy from being delivered to one or more components of the IMD 200. In embodiments, the power manager 216 may control the operation of the deactivation element 222.

The deactivation element 222, which may include one or more circuit elements that require electric energy to function, may be powered by the power source. For example, as indicated above, the deactivation element 222 may include a fuse that, blows upon being provided with a predetermined amount of energy, thereby permanently preventing electrical energy from being provided to one or more of the components of the IMD 200. This energy may be provided by the power source 220, in response to a signal from the power manager 216. In other embodiments, the deactivation element 222 may include a switch that requires energy to be activated, which may be provided by the power source 220. In these and other implementations, as the power source 220 becomes depleted, it may reach a condition in which it does not include enough power to activate the deactivation element 222. According to embodiments, a predetermined amount, or range, of energy may be sequestered for use in activating the deactivation element 222.

The co-implanted device 202 includes a communications component 224 having circuits and one or more transmitters and/or receivers for communicating wirelessly with the seed 200. The communications component 212 of the IMD 200 includes a transceiver 226 and an antenna 228 (or multiple antennae) that work together to facilitate wireless communication 230 with the co-implanted device 202, which may include one or more implantable co-implanted devices (e.g., the co-implanted device 106 depicted in FIG. 1) and/or an external device (e.g., the external device 108 depicted in FIG. 1). In embodiments, the communications component 212 may also facilitate communications with other IMDs 200 (e.g., other seeds) such as, for example, to facilitate coordinated operations between the IMDs. According to various embodiments, the communications component 212 may include one or more transmitters, receivers, transceivers, transducers, and/or the like, and may be configured to facilitate any number of different types of wireless communication such as, for example, radio-frequency (RF) communication, microwave communication, infrared communication, acoustic communication, inductive communication, conductive communication, and/or the like. The communications component 224 may, in addition to facilitating wireless (e.g., RF, microwave, acoustic, etc.) communication with the IMD 200, facilitate wireless communication with an external device (e.g., the external device 130 depicted in FIG. 1), such as a programming device, such that information may be provided to the co-implanted device 202 or supplied to the external device. In embodiments, the communications component 224 may include an antenna disposed on or in the co-implanted device 202 or on a distal portion of an attached lead (not shown).

In an implementation, the co-implanted device 202 includes a controller 232 that may include, for example, a processing unit, a pulse generator, and/or the like. The controller 232 may be a programmable micro-controller or microprocessor, and may include one or more programmable logic devices (PLDs) or application specific integrated circuits (ASICs). The controller 232 may execute instructions and perform desired tasks as specified by the instructions. The controller may also be configured to store information in the memory 234 and/or access information from the memory 234. The memory 234 may include volatile and/or non-volatile memory, and may store instructions that, when executed by the controller 232 cause methods and processes to be performed by the co-implanted device 202. For example, in embodiments, the controller 232 may process instructions and/or data stored in the memory 234 to control delivery of an electrical stimulation therapy by the IMD 200. Additionally, the co-implanted device 202 may sense physiological parameters and/or deliver therapy using a sensor/therapy circuit 236 that may be coupled, for example, to electrodes 238 and 239, a sensor (not shown), or a combination of these. In embodiments, the sensor/therapy circuit 236 may actually include multiple circuits. The memory 234 may be used to store pacing parameters and sensed information according to some implementations. The co-implanted device 202 may also include a power source (e.g., a battery) (not shown) that supplies power to the circuits and components of the co-implanted device 202. In some implementations, the controller 232 may include memory as well. Although the present system is described in conjunction with a co-implanted device 202 having a microprocessor-based architecture, it will be understood that the co-implanted device 202 (or other device) may be implemented in any logic-based integrated circuit architecture, if desired.

The controller 232 may include digital-to-analog (D/A) converters, analog-to-digital (A/D) converters, timers, counters, filters, switches, etc. (not shown). The controller 232, sensor/therapy circuit 236 (e.g., sensing circuits), memory 234, and communications component 224 may work together to control communication between the co-implanted device 202 and one or more leadless electrode assemblies (e.g., IMD 200) to facilitate providing pacing stimuli to the heart. In an implementation, the controller 232 may encode information, such as a unique identifier, pacing threshold information, pulse width information, pacing trigger signals, demand pacing information, pace timing information, and the like, to be transmitted to the seed 200.

Information from sense circuits included in the sensor/therapy circuit 236 may be used to adjust pacing or communications parameters. The sense circuits may amplify and filter signals sensed from sensors positioned in the right or left atrium, or in the right or left ventricle, or from sensors on an external surface of the pacing controller. As is conventional, the sense circuits may include one or more A/D converters. The sensors may be attached to leads implanted within, on, or near the heart, and in some implementations the seed 200 may include sensors and may transmit sensed information to the co-implanted device 202 directly or through a lead that includes a receiver. In some implementations, the seed electrodes that deliver pacing energy to the tissue are the same as the sense electrodes used to sense the local electrical voltage at the pacing site. In these cases, sensing may be paused when pacing energy is being delivered. Similarly, the transmitter/receiver that receives communications may be the same as the transmitter/receiver that sends sensed information back to the co-implanted device 202, according to some implementations. In these cases, outgoing transmissions may be paused when communications are being received. The sensor/therapy circuit 236 of the co-implanted device 202 may include, for example, one or more can or housing electrodes disposed on an exterior surface of the co-implanted device 202.

In embodiments, for example, the controller 232 may receive, via the communications component 224, an indication of an EOL condition corresponding to an IMD 200, which the controller 232 may store in the memory 234. Based on the indication of the EOL condition of the IMD 200, the controller 232 may determine a modified therapy program and/or communication structure associated with additional IMDs and provide, via the communications component 224, operational parameters corresponding to the new program and/or structure to the additional IMDs, an external device, and/or the like. In this manner, therapy programs and communication structures may be modified to compensate for the loss of an IMD 200 such as, for example, when the power source of an IMD 200 depletes such that the IMD 200 reaches an EOL condition.

The illustrative IMD 200 and co-implanted device 202 shown in FIG. 2 are not intended to suggest any limitation as to the scope of use or functionality of embodiments of the invention disclosed throughout this document. Neither should the illustrative IMD 200 and co-implanted device 202 be interpreted as having any dependency or requirement related to any single component or combination of components illustrated therein. For example, in embodiments, the illustrative IMD 200 may include additional components such as, for example, a sensor circuit (not illustrated). Additionally, any one or more of the components depicted in FIG. 2 can be, in embodiments, integrated with various ones of the other components depicted therein (and/or components not illustrated). Any number of other components or combinations of components can be integrated with the illustrative IMD 200 and/or co-implanted device 202 depicted in FIG. 2, all of which are considered to be within the scope of this disclosure.

Figure 3:
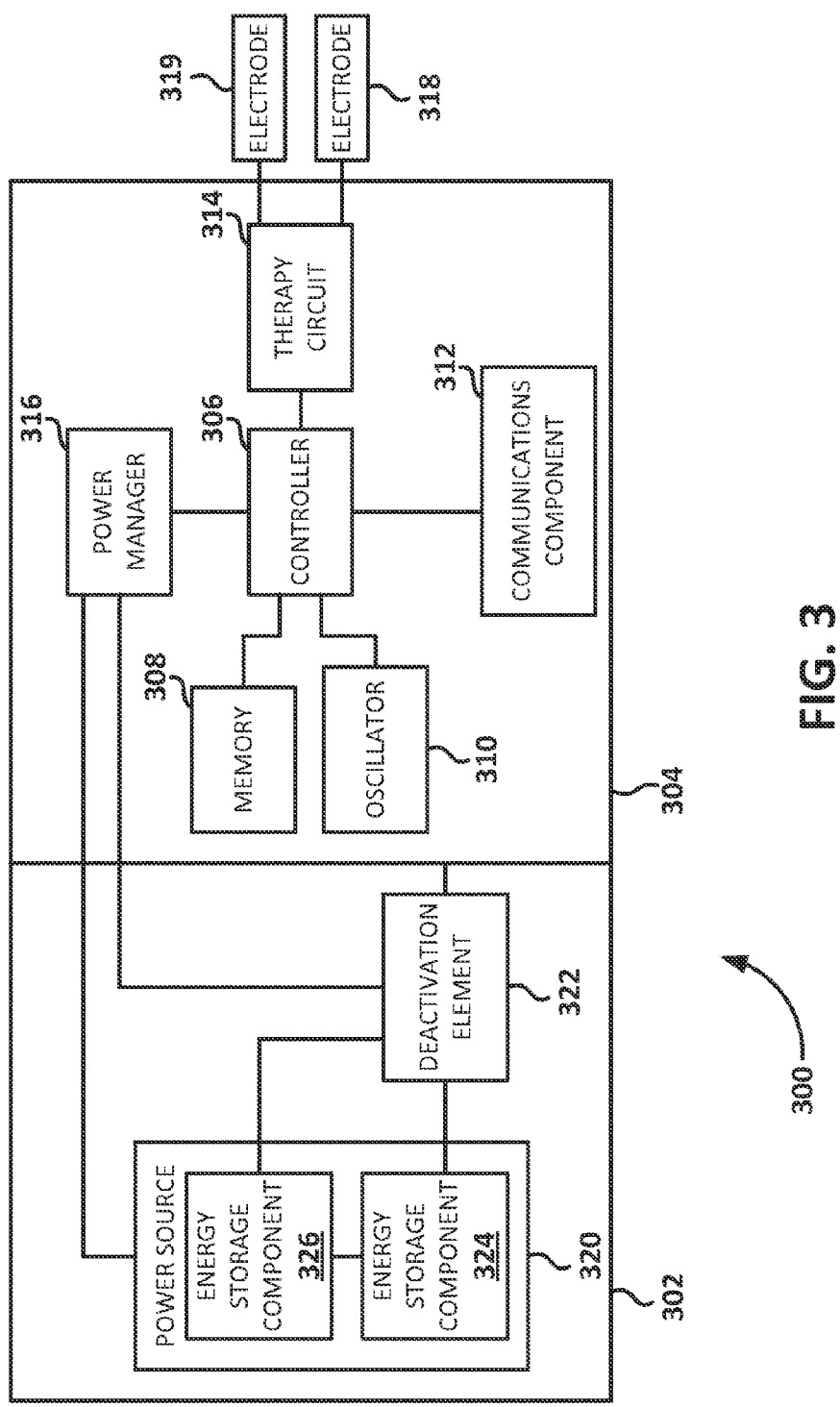
FIG. 3 is a schematic block diagram of an IMD, in accordance with embodiments of the invention.

FIG. 3 is a schematic block diagram of an IMD 300 illustrating aspects of embodiments of the invention. As shown in FIG. 3, the IMD 300 includes a power component 302 that powers operational circuitry 304 of the IMD 300. The operational circuitry 304 includes a controller 306 coupled to a memory 308. An oscillator 310 coupled to the controller 306 may be used as a clocking mechanism to provide timing functions to the controller 306. In embodiments, other types of clocking mechanisms may be used as well as, or in addition, to the oscillator 310. The operational circuitry 304 also includes a communications component 312, a therapy circuit 314, and a power manager 316. As shown in FIG. 3, the therapy circuit 314 is coupled to electrodes 318 and 319 and is configured to provide stimulation energy to the electrodes, which, in turn, provide the energy to a patient's body (e.g., a location in a patient's heart). According to embodiments, the IMD 300 may include more than two electrodes. Additionally, the communications component 312 may be similar to the communications component 212 depicted in FIG. 2 and include a transceiver and an antenna. In embodiments, any number of the components illustrated in FIG. 3 may be, include, or be similar to, similarly named components depicted in FIG. 2. The IMD 300 may include any number of additional components as well such as, for example, a sensor circuit.

As shown in FIG. 3, the power component 302 includes a power source 320 coupled to a deactivation element 322. The illustrated power source 320 includes a first energy storage component 324 and a second energy storage component 326. According to embodiments, the first energy storage component 324 may include, for example, a battery, and may be configured to provide electrical energy to any one or more of the operational circuitry 304 of the IMD 300. The second energy storage component 326 may include, for example, a capacitor and/or an additional battery, and may be configured to store a predetermined amount, or range, of electrical energy for activating the deactivation element 322. In embodiments, for example, when the power manager 316 detects that an end-of-life (EOL) condition of the IMD 300 is nearing, the power manager 316 may send a signal to the power source 320 to cause a predetermined amount, or range, of electrical energy to be transferred from the first energy storage component 324 to the second energy storage component 326, which may store the energy until receiving a signal from the power manager 316 that causes the second energy storage component 326 to provide at least a portion of the stored electrical energy to the deactivation element 322, thereby activating the deactivation element 322.

In embodiments, the power manager 316 may be configured to enter a pre-EOL state in which it is configured to cause deactivation only upon the satisfaction of a trigger condition. In embodiments, for example, the trigger condition may include detecting that the first energy storage component 324 has depleted beyond a predetermined threshold; detecting an abnormality or interruption in the functionality of the therapy circuit 314, the communications component 312, the controller 306, and/or the oscillator 310; receiving a signal from a device external to the IMD 300 (e.g., another IMD, a control device, an external programmer, an external magnet, and/or the like); determining that a certain event has not occurred (e.g., determining that a predetermined signal has not been received within the passage of a certain amount of time); and/or the like.

Upon detecting the occurrence of the trigger condition, the power manager 316 may send a signal to the power component to cause the energy stored in the second energy storage component 326 to be provided to the deactivation element 322, which may be electronically, logically, and/or communicatively coupled to any one or more of the components of the operational circuitry 304 of the IMD 300. In embodiments, the transfer of energy to the deactivation element 322 may cause the deactivation element 322 to enter an EOL state, in which the deactivation element 322 prevents electrical energy from being delivered to one or more components of the IMD 300. For example, the deactivation element 322 may include a fuse or switch that interrupts a conduction path between the first energy storage component 324 and the therapy circuit 314, the communications component 312, the controller 306, and/or the oscillator 310. In embodiments, the deactivation element 322 may include a parasitic circuit that further depletes the first energy storage component 324 such as, for example, a crowbar mechanism. A crowbar mechanism may include any number of different types of circuits configured to drain energy from the first energy storage component 324, thereby preventing delivery of energy from the first energy storage component 324 to any other component.

Figure 13:
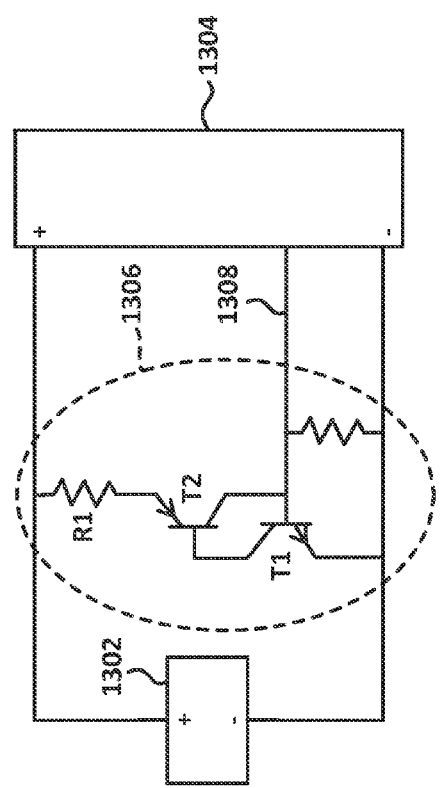
FIG. 13 is a schematic circuit diagram depicting an illustrative circuit arrangement for an implantable medical device, in accordance with embodiments of the invention.
Figure 14:
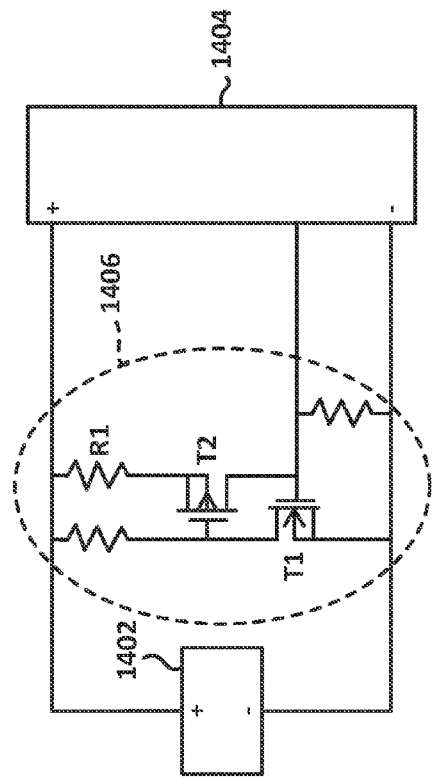
FIG. 14 is another schematic circuit diagram depicting an illustrative circuit arrangement for an implantable medical device, in accordance with embodiments of the invention.

FIGS. 13 and 14 are schematic circuit diagrams depicting illustrative examples of crowbar mechanisms that may, in embodiments, be utilized as a deactivation element 322. FIG. 13 depicts a bipolar circuit arrangement in which a power source 1302 (e.g., a battery) provides electrical power (e.g., via current) to operational circuitry 1304 (e.g., the operational circuitry 304 depicted in FIG. 3). A crowbar mechanism 1306 is disposed between the power source 1302 and the operational circuitry 1304 and may be utilized as a deactivation element (e.g., the deactivation element 322 depicted in FIG. 3) to prevent power from being delivered to the operational circuitry 1304. A trigger connection 1308 is used to provide a trigger signal (e.g., a deactivation signal) to a first (NPN) transistor T1. The trigger signal activates T1, which causes a second (PNP) transistor T2 to activate, thereby draining power from the power source 1302. The crowbar mechanism 1306 may be, or include, a traditional silicone-controlled rectifier (SCR), discrete transistors T1 and T2, or the like. The resistor R1, illustrated in FIG. 13, may be selected to allow rapid depletion of the power source 1302 without allowing depletion that is so rapid that it causes excessive heat. Additionally, R1 may be selected so that the emitter of T2 does not drop to a voltage so low as to prevent T1 and T2 from remaining activated. FIG. 14 depicts a circuit arrangement in which a power source 1402 provides electrical power (e.g., via voltage) to operational circuitry 1404. A crowbar mechanism 1406 is disposed between the power source 1402 and the operational circuitry 1404 and may be utilized as a deactivation element (e.g., the deactivation element 322 depicted in FIG. 3) to prevent power from being delivered to the operational circuitry 1404. The crowbar mechanism 1406 similar to that of FIG. 13; however, in FIGS. 14, T1 and T2 are metal-oxide-semiconductor field-effect transistors (MOSFETs).

Returning to FIG. 3, the IMD 300 may include a rechargeable power source 320 such as, for example, a rechargeable battery. In such implementations, the IMD 300 may be configured to be partially or completely disabled reversibly and then reactivated after the power source 320 has been recharged. To facilitate returning to a particular operational state upon reactivation, the controller 306 may be configured to save one or more operational parameters associated with the IMD 300, which may be accessed upon reactivation. The one or more operational parameters may be stored in the memory 308. The memory 308 may include one or more memory elements such as, for example, a non-volatile memory element, an active memory element, and/or the like. In embodiments, the controller 306 may be configured to store only an indication of an EOL state associated with the IMD 300, while in other embodiments, the controller 306 may be configured to store a number of operational parameters.

Non-volatile memory may be used, for example, to store information even when IMD 300 is completely disabled (e.g., energy is prevented from being delivered to every component of the IMD 300). Active memory elements may be used to store information when the power source 320 maintains an ability to provide some energy during the EOL state of the IMD 300. For example, the first or second energy storage component 324,326 may include enough stored energy to provide to the memory 308. In embodiments, the memory 308 may be an active storage element configured to store an indication of an EOL state of the IMD 300. The indication may include a single bit or multiple bits. In the case of a single bit (or a small number of bits), the memory 308 may include a latch or system of latches. Other techniques for maintaining information associated with an EOL state are contemplated within the scope of embodiments of the invention. For example, in embodiments, upon detecting an EOL condition, the power manager 316 may be configured to cause the IMD 300 to transfer data (e.g., operational parameters, indications of the EOL condition, etc.) to another IMD 300, a control device, an external programmer and/or the like.

Figures 4, 5:
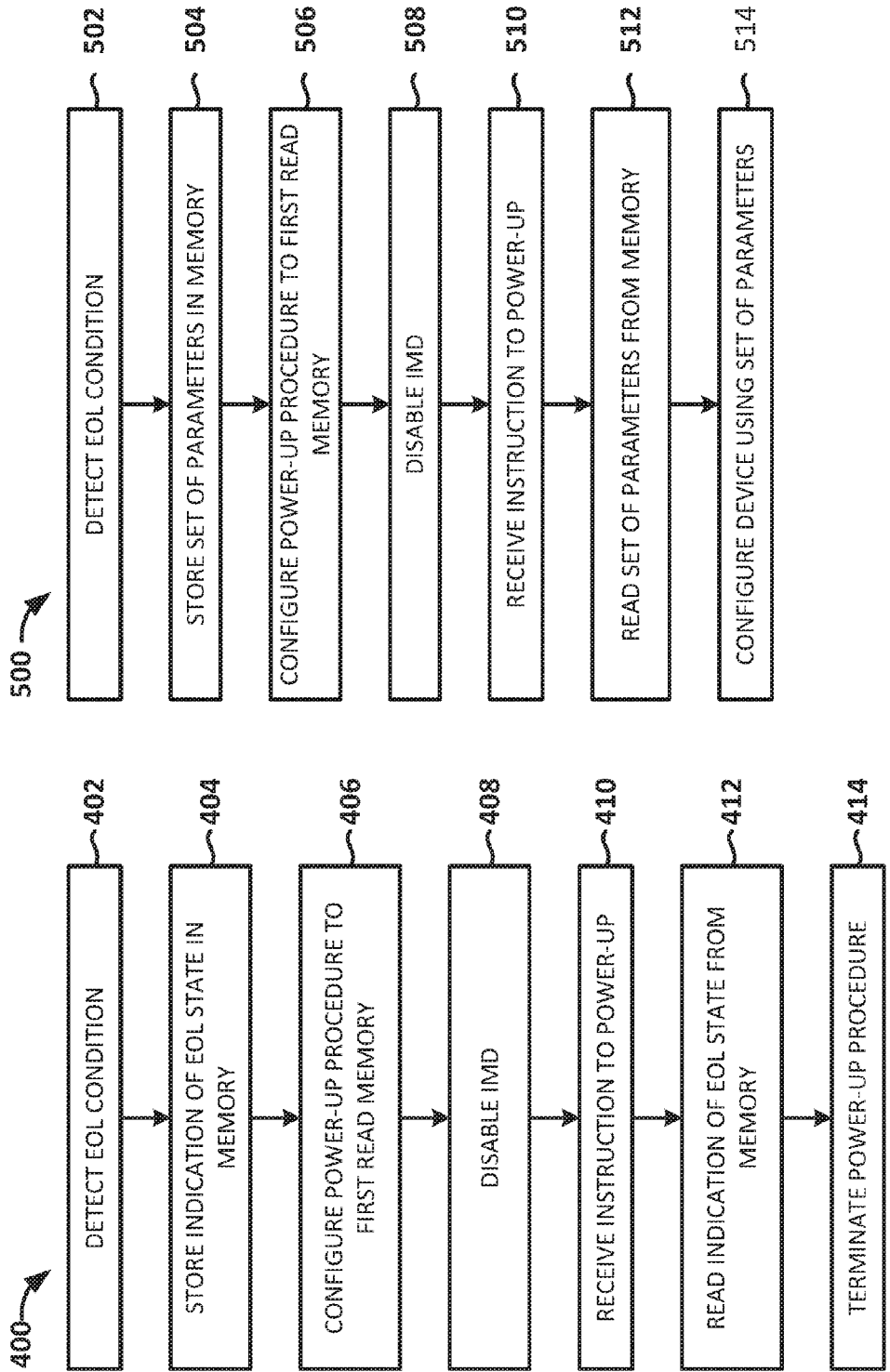
FIG. 4 is a flow diagram depicting an illustrative method of managing an end-of-life state of an IMD, in accordance with embodiments of the invention.
FIG. 5 is another flow diagram depicting an illustrative method of managing an end-of-life state of an IMD, in accordance with embodiments of the invention.

FIG. 4 is a flow diagram depicting an illustrative method 400 of managing an end-of-life (EOL) state of an IMD, in accordance with embodiments of the invention. The IMD may be, or include, the IMD 102 depicted in FIG. 1, the IMD 200 depicted in FIG. 2, and/or the like. In embodiments, the IMD may be a leadless cardiac pacing seed. As shown in FIG. 4, the illustrative method 400 includes detecting an end-of-life (EOL) condition of the IMD (block 402) and, in response, storing an indication of the EOL condition in a memory (block 404). The method 400 also includes configuring a power-up procedure of the IMD such that, when a future activation of the IMD is attempted, the controller first reads the memory containing the indication of the EOL condition (block 406). As depicted in FIG. 4, the IMD is disabled (e.g., by preventing power from being delivered from a power source to one or more components of the operational circuitry of the IMD) (block 408). At some point later, the IMD receives an instruction to power up (e.g., an activation signal) (block 410) and, in response, reads the indication of the EOL state from the memory (block 412). Upon discovering that the IMD has been placed in the EOL state, the controller terminates the power-up procedure (block 414).

FIG. 5 is another flow diagram depicting an illustrative method 500 of managing an EOL state of an IMD, in accordance with embodiments of the invention. According to embodiments, the illustrative method 500 includes detecting an EOL condition of the IMD (block 502) and, in response, storing a set of parameters in a memory (block 504). The method 500 also includes configuring a power-up procedure such that, when a future activation of the IMD is attempted, the controller reads the parameters from the memory (block 506). The IMD is disabled (e.g., by preventing power from being delivered from a power source to one or more components of the operational circuitry of the IMD) (block 508). At some point later, the IMD receives an instruction to power up (block 510) and, in response, reads the stored set of parameters from the memory (block 512). As shown, the device configures itself for operation based on the stored parameters (block 514).

As described above, embodiments of the invention include a deactivation element that facilitates deactivating one or more components of an IMD. The deactivation element may, in embodiments, be configured to selectively disable certain components of an IMD, while allowing other components to remain active. In embodiments, the deactivation element may selectively disable components by preventing power from being delivered, by the power source, to the selected components. This may be accomplished by using a deactivation element that includes, for example, a number of switches, latches, gates, and/or the like.

Figure 6:
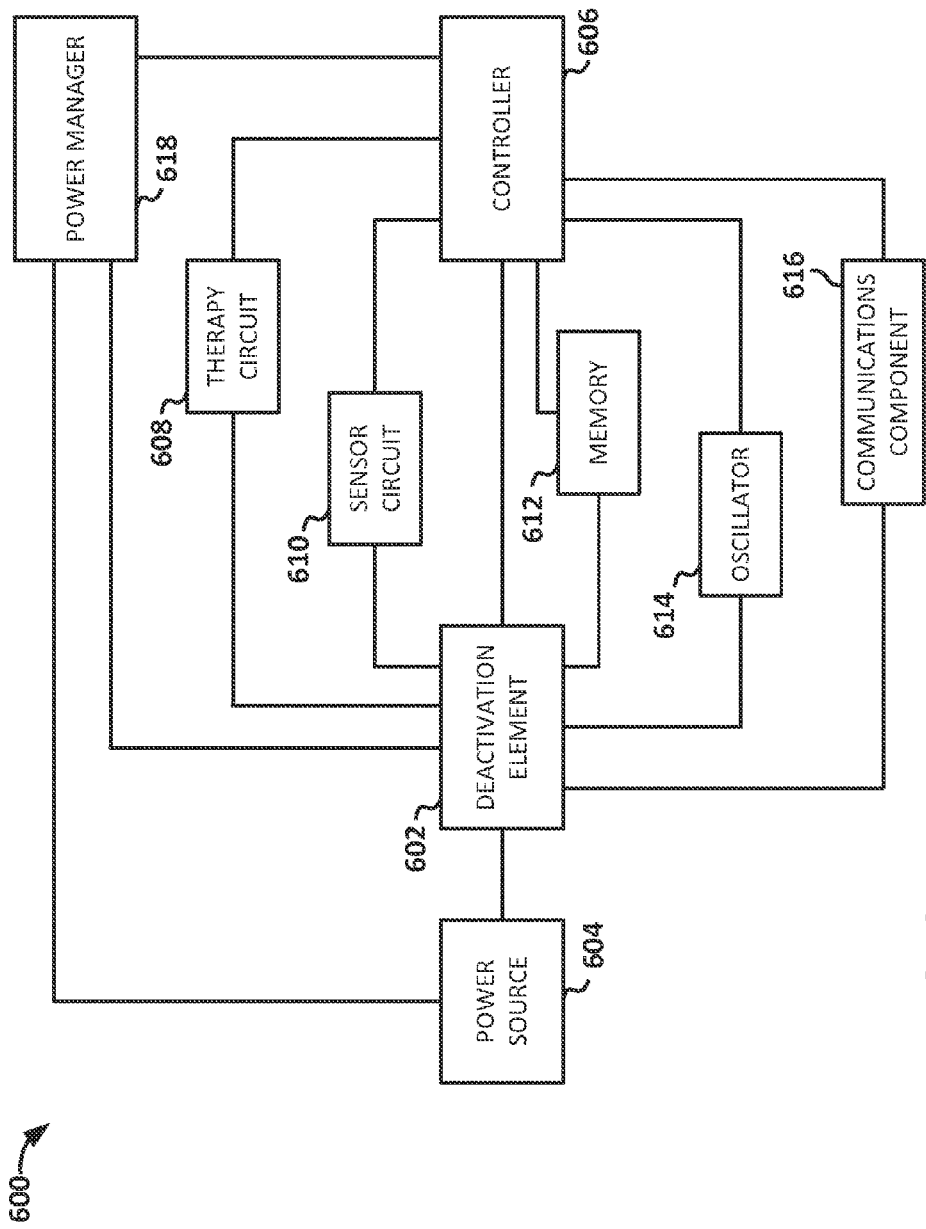
FIG. 6 is a schematic block diagram of an IMD, in accordance with embodiments of the invention.

FIG. 6 is a schematic block diagram depicting an illustrative IMD 600 having a deactivation element 602 capable of selectively disabling components of the IMD 600, in accordance with embodiments of the invention. The IMD 600 may include any number of different types of IMDs such as for example, implantable sensors, implantable stimulators (e.g., leadless cardiac pacing seeds), implantable control devices, and/or the like. As shown in FIG. 6, the deactivation element 602 is electrically coupled to a power source 604 and provides selectable current paths to a controller 606, a therapy circuit 608, a sensor circuit 610, a memory 612, an oscillator 614, and a communications component 616. A power manager 618 may be configured to monitor the power source 604 and/or one or more other components to detect an end-of-life (EOL) condition. In the illustrated embodiment, the power manager 618 monitors components such as the therapy circuit 608, the sensor circuit 610, and the communications component 616 by accessing information from the controller 606 corresponding to the operation of those components. In embodiments, the power manager 618 may include a direct connection to the components that it monitors.

The illustrative IMD 600 shown in FIG. 6 is not intended to suggest any limitation as to the scope of use or functionality of embodiments of the invention disclosed throughout this document. Neither should the illustrative IMD 600 be interpreted as having any dependency or requirement related to any single component or combination of components illustrated therein. For example, in embodiments, the illustrative IMD 600 may include additional components such as, for example, additional sensor circuits (not illustrated). Additionally, any one or more of the components depicted in FIG. 6 can be, in embodiments, integrated with various ones of the other components depicted therein (and/or components not illustrated). Any number of other components or combinations of components can be integrated with the illustrative IMD 600 depicted in FIG. 6, all of which are considered to be within the scope of this disclosure.

In an example embodiment, the power manager 618 may monitor the therapy circuit 608 and detect an EOL condition. The EOL condition may include, for example, a condition in which the therapy circuit 608 is delivering erratic or otherwise unexpected therapy. Upon detecting the EOL condition, the power manager 618 may send a signal to the deactivation element 602 to cause the deactivation element 602 to prevent power from being delivered from the power source 604 to the therapy circuit 608. The deactivation element 602 may continue to allow power to flow, however, to any number of the other components of the IMD 600. As the power source 604 continues to deplete, the power manager 618 may detect another EOL condition by detecting erratic or otherwise unexpected behavior by the communications component 616. Upon detecting the EOL condition, the power manager 618 may send a signal to the deactivation element 602 to cause the deactivation element 602 to prevent power from being delivered from the power source 604 to the communications component 616.

In embodiments, the deactivation element may selectively disable components by logically disabling the selected components. This may be accomplished by using a deactivation element that includes, for example, isolated logic circuits, sets of instructions that may be executed by the processor, and/or the like. In aspects of this implementation, for example, all of the components of the IMD 600 depicted in FIG. 6 may be communicatively coupled to the controller, which executes the deactivation element 602 to logically disable selected components.

Figure 7:
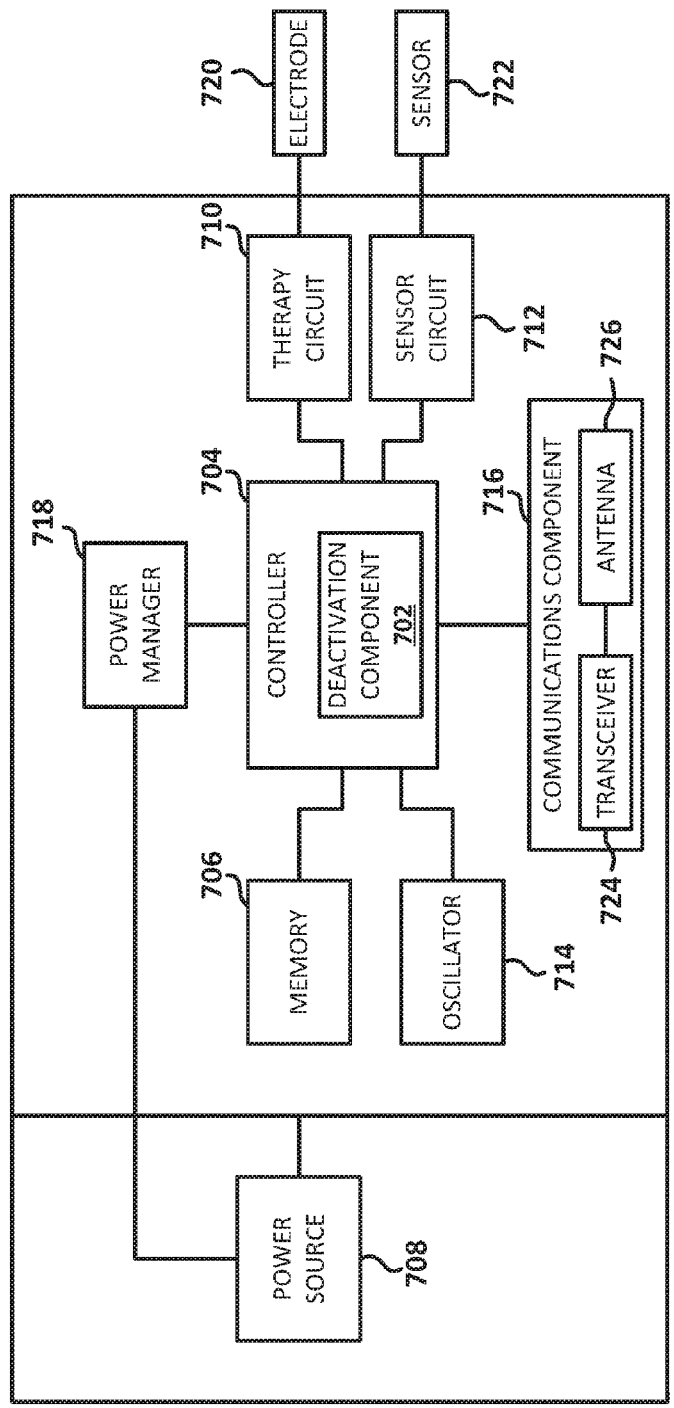
FIG. 7 is a schematic block diagram of an IMD, in accordance with embodiments of the invention.

FIG. 7 is a schematic block diagram depicting an illustrative IMD 700 having a deactivation element 702 capable of selectively disabling components of the IMD 700, in accordance with embodiments of the invention. The IMD 700 may include any number of different types of IMDs such as for example, implantable sensors, implantable stimulators (e.g., leadless cardiac pacing seeds), implantable control devices, and/or the like. As shown in FIG. 7, the deactivation element 702 is a logical module executable by a controller 704. For example, the deactivation element 702 may include a set of computer-readable instructions that are stored in a memory 706 and that, when accessed from the memory 706 and executed by the controller 704, facilitate logically disabling any one or more components of the IMD 700.

As shown in FIG. 7, a power source 708 (e.g., a battery) provides power to the controller 704, a therapy circuit 710, a sensor circuit 712, the memory 706, an oscillator 714, and a communications component 716. A power manager 718 may be configured to monitor the power source 708 and/or one or more other components to detect an end-of-life (EOL) condition. As shown in FIG. 7, the therapy circuit 710 is coupled to an electrode 720 and is configured to cause electrical pacing energy to be discharged from the electrode 720. Similarly, the sensor circuit 712 is coupled to a sensor 722, which, in embodiments, may be an electrode, a pressure sensor, and optical sensor and/or the like. In embodiments, the therapy circuit 710 may be coupled to more than one electrode 720. In the illustrated embodiment, the power manager 718 monitors components such as the therapy circuit 710, the sensor circuit 712, and the communications component 716 by accessing information from the controller 704 corresponding to the operation of those components. In embodiments, the power manager 718 may include a direct connection to the components that it monitors.

The illustrative IMD 700 shown in FIG. 7 is not intended to suggest any limitation as to the scope of use or functionality of embodiments of the invention disclosed throughout this document. Neither should the illustrative IMD 700 be interpreted as having any dependency or requirement related to any single component or combination of components illustrated therein. For example, in embodiments, the illustrative IMD 700 may include additional components such as, for example, additional sensor circuits (not illustrated). Additionally, any one or more of the components depicted in FIG. 7 can be, in embodiments, integrated with various ones of the other components depicted therein (and/or components not illustrated). Any number of other components or combinations of components can be integrated with the illustrative IMD 700 depicted in FIG. 6, all of which are considered to be within the scope of this disclosure.

In an example embodiment, the power manager 718 may monitor the therapy circuit 710 and detect an EOL condition. The EOL condition may include, for example, a condition in which the therapy circuit 710 is delivering erratic or otherwise unexpected therapy. Upon detecting the EOL condition, the power manager 718 may send a signal to the deactivation element 702 to cause the deactivation element 702 to prevent power from being delivered from the power source 708 to the therapy circuit 710. The deactivation element 702 may continue to allow power to flow, however, to any number of the other components of the IMD 700. As the power source 702 continues to deplete, the power manager 718 may detect another EOL condition by detecting erratic or otherwise unexpected behavior by the communications component 716.

As shown in FIG. 7, the communications component 716 includes a transceiver 724 and an antenna 726. According to embodiments, the communications component 716 may include, instead of a transceiver, a transmitter, a receiver, or both. An EOL condition may be one in which the transceiver 724 (or transmitter) is not receiving sufficient power to accurately modulate an outgoing signal, thereby causing errors and/or gaps in transmitted communication. Similarly, an EOL condition may be one in which the transceiver 724 (or receiver) is not receiving enough power to accurately demodulate an incoming signal, thereby causing errors and/or gaps in received communication. Upon detecting the EOL condition, the power manager 718 may send a signal to the deactivation element 702 to cause the deactivation element 702 to prevent power from being delivered from the power source 708 to the communications component 716.

In embodiments, a power manager (e.g., the power manager 618 depicted in FIG. 6 or the power manager 718 depicted in FIG. 7) may be configured, as in the examples above, to selectively disable components of the IMD as EOL conditions are detected. In this manner, embodiments facilitate disabling certain functions of an IMD with minimal disruption to other functions. Additionally, in embodiments, sets of components (e.g., input circuits, output circuits, etc.) may be selectively disabled in stages, either electronically or logically. Disabling the IMD in stages may also facilitate allowing enough time for information to be stored, transmitted, or received. Various algorithms, processes, protocols, and the like may be used to implement embodiments of a staged deactivation. FIG. 8 illustrates an example of such a process.

FIG. 8 is a flow diagram depicting an illustrative method 800 of deactivating an IMD in accordance with embodiments of the invention. In the illustrated example, the IMD may be, for example, a leadless pacing seed that includes at least a therapy circuit, a sensor circuit, and a communications component. As shown in FIG. 8, the illustrative method 800 includes detecting an end-of-life (EOL) condition (block 802). In embodiments, a power manager (e.g., the power manager 618 depicted in FIG. 6 or the power manager 718 depicted in FIG. 7) may be configured to detect an EOL condition associated with the IMD by monitoring the power source or one or more components that consume power from the power source. Monitoring the power source, in embodiments, may include one or more mechanisms and/or processes for monitoring power levels that are stored in, and/or are outputted from, the power source. Monitoring other components, in embodiments, may include one or more mechanisms and/or processes for monitoring the functionality of those components to identify erratic, unreliable, or otherwise unexpected behavior.

Embodiments of the illustrative method 800 further include preventing power delivery to the therapy circuit (block 804). In response to detecting the EOL condition, the power manager may provide a signal to a deactivation element (e.g., the deactivation element 602 depicted in FIG. 6 or the deactivation element 702 depicted in FIG. 7) that causes the deactivation element to prevent power from flowing from the power source to the therapy circuit. In the illustrative method 800, while continuing to monitor components of the IMD, the power manager detects an insufficient power condition (e.g., another EOL condition) associated with the communications component (806). For example, the power manager may detect that the communications component is communicating a number of errors that exceed a threshold, is transmitting random packets, or the like. In response to detecting the EOL condition, the power manager may send a signal to the deactivation element to cause it to prevent power delivery to the communications component (block 808). During further monitoring, the power manager may detect an insufficient power condition for the sensor circuit (block 810) and, in response, may cause the deactivation element to prevent power delivery to the sensor circuit (block 812). In embodiments, the order in which elements are deactivated may be different than the order described above. For example, in embodiments, the therapy circuit might be disabled last in order to provide therapy to the patient for as long as possible.

FIG. 9 depicts another illustrative method 900 of deactivating an IMD in accordance with embodiments of the invention. As shown in FIG. 9, the illustrative method 900 includes determining that an end-of-life (EOL) condition of the IMD is nearing (block 902) and setting an EOL state trigger (block 904). According to embodiments, the EOL state trigger may include a condition or conditions that, when satisfied, result in the deactivation element deactivating the IMD. The condition may include passage of a certain amount of time, a predetermined energy level in the power source, an occurrence of a certain action (e.g., receipt of a signal from another IMD, a control device, or an external device), a non-occurrence of a certain action within a certain amount of time, and/or the like. In the illustrative method 900, the EOL state trigger is detected (block 906) and, in response, the IMD is disabled (block 908).

Figure 10:
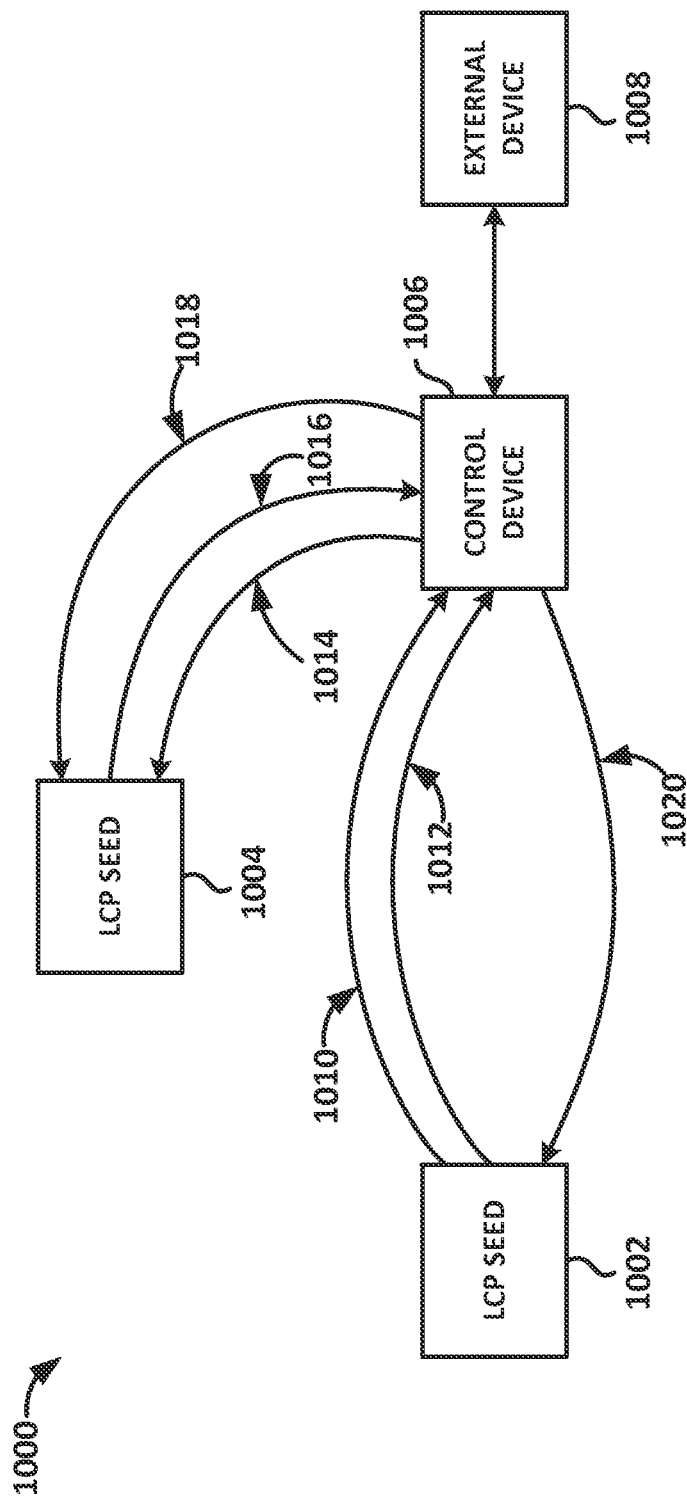
FIG. 10 is a schematic block diagram depicting an illustrative implantable leadless pacing system, in accordance with embodiments of the invention.

As indicated previously, embodiments of the invention include an IMD such as a leadless pacing seed that operates within a system having one or more additional leadless pacing seeds. Embodiments include modifying a therapy program and/or communication structure of the remaining seeds when a first seed reaches an end-of-life condition. In this manner, the system mitigates effects of the loss of the use of the first seed. FIG. 10 is a block schematic diagram depicting illustrative operations of a leadless pacing system 1000 configured to mitigate for the loss of a pacing seed, in accordance with embodiments of the invention. According to various embodiments, the system 1000 depicted in FIG. 10 may include a system for providing cardiac resynchronization therapy (CRT), defibrillation therapy, and/or the like. Although the system 1000 is described in the context of a cardiac stimulation system, the system 1000 may represent any number of different types of systems such as, for example, a neurostimulation system, an electrocardiograph sensing system, and/or the like.

The illustrative system 1000 includes a first leadless cardiac pacing (LCP) seed 1002, a second LCP seed 1004, and a control device 1006. The first and second LCP seeds 1002 and 1004 may be any number of different types of leadless pacing seeds. In embodiments, the seeds 1002 and 1004 may be similar to the IMDs described previously such as, for example, the IMD 102 depicted in FIG. 1, the IMD 200 depicted in FIG. 2, and/or the IMD 300 depicted in FIG. 3. The control device 1006 may be similar to the co-implanted device 202 depicted in FIG. 2 and may be, or include, a pacemaker module, a subcutaneous implantable cardioverter defibrillator (S-ICD), and/or the like. The illustrated system 1000 also includes an external device 1008 which may, in embodiments, be an external programmer, a magnet, an interrogation device, and/or the like.

The external device 1008 may be used to communicate with the implantable control device 1006. For example, the external device 1008 may be used to program such parameters as the timing of stimulation pulses in relation to certain sensed electrical activity of the heart, the energy level of stimulation pulses, the duration of stimulation pulses (that is, pulse width), and/or the like. Additional information such as locations of seeds 1002 and 1004 within heart chambers may be programmed, as well as pacing requirements involving one or more of the distributed seeds 1002 and 1004. The external device 1008 may include an antenna to communicate with the control device 1006, using, for example, RF signals. The implantable control device 1006 may accordingly be equipped to communicate with the external device 1008 using, for example, RF signals. Similarly, the control device 1006 may transmit information, such as sensed cardiac patient information, system status information, warning information, and the like, to an external computing device. Physicians or care providers may then monitor the information and make changes as appropriate.

According to embodiments of the system 1000 illustrated in FIG. 10, a dual-chamber therapy may be provided using two LCP seeds 1002 and 1004, in which case each seed 1002 and 1004 may be reliant on the other's behavior. That is, for example, a first seed 1002 may be configured as a "slave" and may be configured to provide therapy in response to a second seed 1004, configured as a "master," providing therapy. In other embodiments, the two LCP seeds 1002 and 1004 may be peer devices in which neither is a master or a slave, though aspects of the operation of each may depend upon aspects of the operation of the other. In embodiments, the synchronization between the first and second seeds 1002 and 1004 may be provided by communications between the two seeds 1002 and 1004 themselves, by a control device 1008, and/or a combination of these. In other embodiments, a number of additional LCP seeds may be utilized for providing any number of different types of therapy such as cardiac resynchronization therapy, anti-tachycardia pacing therapy, neural stimulation therapy, and/or the like.

In embodiments, each of the first and second LCP seeds 1002 and 1004, operating according to a first operational state, may be monitored to detect an end-of-life (EOL) condition associated therewith. For example, each LCP seed 1002 and 1004 may include a power manager (e.g., the power manager 216 depicted in FIG. 2) that monitors a battery and/or one or more components (e.g., operational circuitry) of the seed 1002, 1004. In embodiments, the control device 1006 and/or the external device 1008 may monitor the LCP seeds 1002 and 1004 to detect EOL conditions. When one of the LCP seeds 1002 or 1004 is placed into an EOL state, the other of the seeds 1002 or 1004 may be configured, as described herein, to adjust its therapy and/or communications so as to compensate for the loss of the functionality of the seed 1002 or 1004 that is in an EOL state. In embodiments, the control device 1006 and/or the external device 1008 may be used to facilitate modifying the therapy and/or communications. In other embodiments, the seeds 1002 and 1004 themselves may be configured to adjust operations to compensate for the loss of the other seed or seeds.

FIG. 10 also schematically illustrates an example of a compensation procedure that may be implemented according to embodiments of the invention. As shown in FIG. 10, when an EOL condition associated with the first LCP seed 1002 is detected, a notification signal 1010 may be transmitted to the control device 1006 that indicates that the EOL condition has been detected. The LCP seed 1002 may also transmit information 1012 to the control device 1006 to be used in modifying therapy programs and/or communication structures. Accordingly, the information 1012 may include, for example, operational parameters, communications protocols, physiological parameters sensed by the LCP 1002, and/or the like.

Upon receiving the notification signal 1010 and the information 1012, the control device 1006 may, for example, implement a procedure for resynchronizing therapy and/or communication structures. In embodiments, the control device 1006 may include predetermined modified therapy programs and/or communication structures, calculation modules for determining modified therapy programs and/or communication structures, and/or combinations of these. In the illustrated example, the control device 1006 may determine a modified therapy program that is configured to facilitate providing therapy using only the second LCP seed 1004 and a modified communication structure that facilitates communications between the control device 1006 and only the second LCP seed 1004. In other embodiments, the system 1000 may include a number of additional LCP seeds and the control device 1006 may, for example, be configured to determine a modified therapy program that redistributes therapy duties among the remaining seeds.

The control device 1006 may provide the modified therapy program and/or communication structure via a communication 1014 to the second LCP seed 1004. The LCP seed 1004 may store the modified therapy program and/or communication structure and configure its operational circuitry to implement the modified program/structure, thereby implementing a second operational state. When the second LCP seed 1004 has finished configuring itself to operate according to the second operational state, the second seed 1004 may provide a confirmation signal 1016 to the control device 1006 to indicate to the control device that the second seed 1004 is prepared to operate in the absence of operation of the first LCP seed 1002.

Having received the confirmation signal 1014, the control device 1006 may provide an activation signal 1018 to the second LCP seed 1004 and a deactivation signal 1020 to the first LCP seed 1002. In embodiments, the activation signal 1018 and the deactivation signal 1020 may be provided substantially simultaneously (e.g., in parallel), and, in embodiments, the two signals 1018 and 1020 may be provided sequentially (e.g., in series). According to embodiments, the activation signal 1018 and the deactivation signal 1020 may actually be communicated as a single broadcast communication. In aspects of such implementations, the control device 1006 may provide instructions to the first LCP seed 1002 that configure the first LCP seed 1002 to interpret the broadcast signal as a deactivation signal, and instructions to the second LCP seed 1004 that configure the second LCP seed 1004 to interpret the broadcast signal as an activation signal.

According to embodiments, the control device 1006 may provide any number of various types of information to the external device 1008 regarding the state of the system 1000. For example, in an embodiment, the control device 1006 may provide an indication to the external device 1008 that the control device 1006 has received the confirmation signal 1014 from the second LCP seed 1004. The external device 1008 may provide instructions to the control device 1006 that cause the control device 1006 to be configured to wait to receive an implementation signal from the external device 1008 before sending the activation signal 1018 and deactivation signal 1020. In this manner, the system 1000 may be prepared to transition to a system state in which the first LCP seed 1002 is disabled and the second LCP seed 1004 operates according to the second operational state. When the implementation signal is received from the external device 1008, the control device 1006 may provide the activation signal 1018 and the deactivation signal 1020 to the second LCP seed 1004 and the first LCP seed 1002, respectively. In embodiments, the implementation signal may be triggered by satisfaction of a condition, a manual input provided by a clinician, or the like.

Upon receiving the activation signal 1018, the second LCP seed 1004 may process the signal 1018 and, in response, implement the second operational state. In this manner, the second LCP seed 1004 may begin providing therapy according to the modified therapy program and may begin communicating with the control device 1006 according to the modified communication structure. Upon receiving the deactivation signal 1020, the first LCP seed 1002 may process the signal 1020, which may cause a deactivation element to disable the first LCP seed 1002. As discussed above, the deactivation element of the first LCP seed 1002 may disable the first LCP seed 1002 by logically disabling one or more components thereof (e.g., a therapy circuit, a communications component, an oscillator, etc.), preventing power from being delivered to one or more components (e.g., operational circuitry) thereof, blowing a fuse, crow-barring the power source, and/or the like. For example, in embodiments, the deactivation element of the first LCP seed 1002 may initially disable the therapy circuit, while leaving the communications component operational so that the first LCP seed 1002 can provide a confirmation of deactivation (not shown) to the control device 1006. In other embodiments, the deactivation element may disable the therapy circuit and the communications component.

In embodiments, the first and second LCP seeds 1002 and 1004 deliver pacing therapy in a dual-chamber pacing (DDD) mode in which the seed 1002 is implanted such that at least one of its electrodes contacts atrial tissue and in which the seed 1004 is implanted such that at least one of its electrodes contacts ventricular tissue. Upon the depletion of, for example, the power source of the seed 1002, the seed 1004 alters its therapy from pacing in a DDD mode to pacing in a ventricular pacing (VVI) mode. In another embodiment, the first and second LCP seeds 1002 and 1004 deliver cardiac resynchronization therapy in which the seed 1002 is implanted such that at least one of its electrodes contacts left ventricular tissue and in which the seed 1004 is implanted such that at least one of its electrodes contacts right ventricular tissue. Upon depletion of, for example, the power source of the seed 1002, the seed 1004 alters its therapy from cardiac resynchronization therapy to bradycardia therapy and paces in a right ventricular-only VVI mode.

Figure 11:
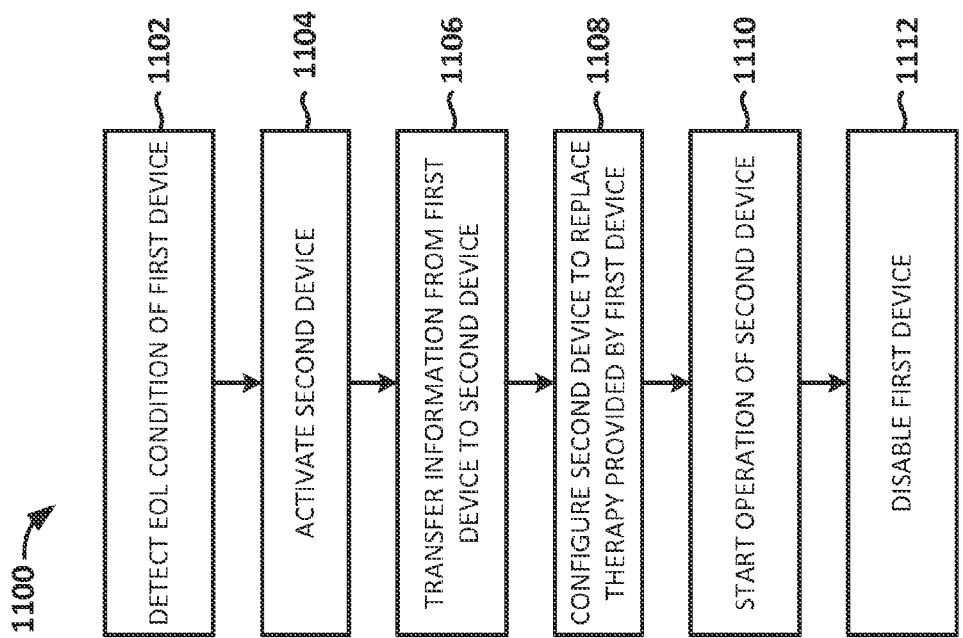
FIG. 11 is a flow diagram depicting in illustrative method of replacing a first IMD with a second IMD.

FIG. 11 is a flow diagram depicting an illustrative method 1100 of deactivating a first IMD that is being replaced by a second IMD, in accordance with embodiments of the invention. As shown in FIG. 11, the illustrative method 1100 includes detecting an end-of-life condition (EOL) of a first device (block 1102) and, in response, activating a second device (block 1104). In embodiments, the second device may be implanted before an EOL condition of the first device is anticipated and may be initially in a dormant state. The dormant state may, for example, be characterized by a state in which the second device has only enough components activated so that the second device can receive a signal from the first device, from an external device, and/or the like.

Accordingly, the second device may be activated by a signal sent from the first device to the second device. Activation of the second device may place the second device in a stand-by state, in which the second device can receive information and/or additional instructional signals from the first device, a control device, an external device, and/or the like. In embodiments, the second device may be activated by a signal sent from the control device or an external device.

In response to detecting the EOL condition of the first device, the first device transfers information to the second device (block 1106). In embodiments, the information transferred to the second device may include operational parameters such as therapy parameters, physiological parameters, and the like. The method 1100 further includes configuring the second device to replace the therapy provided by the first device (block 1108). For example, the second device may process the information received from the first device to generate a set of operational parameters that may be used to implement an operational state in which the second device provides therapy in a manner that replaces the therapy provided by the first device.

Once configured, the second device is activated, to begin operation according to the operational state (block 1110) and the first device is disabled (block 1112). In embodiments, the second device may be activated automatically upon receiving and processing the information from the first device. In other embodiments, the second device may be activated upon receiving an activation signal from a control device and/or an external device. Similarly, the first device may be disabled automatically after sending the information to the second device or upon receiving a confirmation signal from the second device, a control device, and/or an external device.

Figure 12:
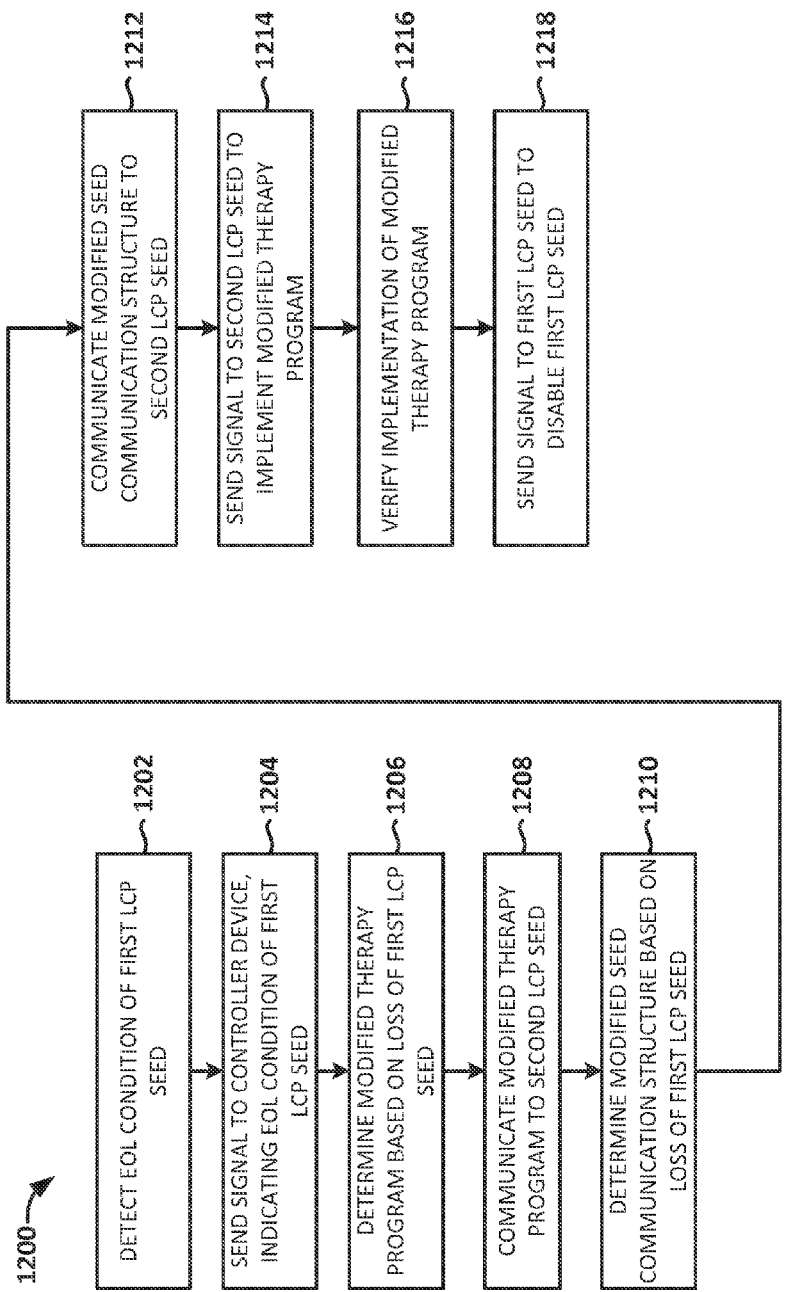
FIG. 12 is a flow diagram depicting an illustrative method of mitigating the effects from a loss of a leadless pacing seed, in accordance with embodiments of the invention.

FIG. 12 is a flow diagram depicting an illustrative method 1200 of deactivating a leadless pacing seed that is part of a leadless pacing system, in accordance with embodiments of the invention. As shown in FIG. 12, the illustrative method 1200 includes detecting an end-of-life (EOL) condition of a first pacing seed (block 1202) and, in response, sending a signal to a control device that indicates the EOL condition of the first pacing seed (block 1204). In embodiments, the first pacing seed includes a power manager that monitors the power source and/or one or more components (e.g., operational circuitry) of the seed to detect an EOL condition. Upon detecting the EOL condition, the power manager may cause a controller to communicate, via a communications component, a signal to a control device.

As illustrated in FIG. 12, the control device determines a modified therapy program based on an anticipated loss of the first pacing seed (block 1206) and communicates the modified therapy program to a second pacing seed (block 1208). According to various embodiments, the control device includes a processor that executes a set of routines to determine the modified therapy program. In embodiments, the control device may include a memory that stores a set of modified therapy program, and the control device may select the appropriate program based on an identification of the particular seed that has reached an EOL condition. A modified therapy program may include different sets of operational parameters for each of a number of seeds, as described above with respect to FIG. 11, and the control device may communicate each set of operational parameters to the appropriate seed.

In the illustrative method 1200, the control device also determines a modified seed communication structure based on the anticipated loss of the first pacing seed (block 1210) and communicates the modified seed communication structure to the second pacing seed (block 1212). This modified communication structure may specify communication flows, protocols, and/or the like.

In embodiments, prior to the anticipated loss of the first pacing seed (prior to block 1202) the second pacing seed operates in a low-power communication mode. The low-power communication mode limits the energy used for communication before the second seed is delivering therapy. In order to achieve the lower power in this mode, the second seed's communication components may, for example, operate at a lower receive and/or transmit bit rate. After an EOL condition has been detected, the communication structure of the second seed may be modified to a higher-power mode that can support the communication requirements of the second seed while it provides therapy.

As shown in FIG. 12, the control device sends a signal to the second seed to cause the second seed to implement the modified therapy program (block 1214). In embodiments, the system may include a number of additional seeds to which the control device has provided modified therapy programs and communication structures and the control device may send each of these seeds a signal to cause implementation of the programs and structures. In embodiments, for example, the control device may broadcast a signal that, when received by any of the seeds, causes the seed to implement modified therapy programs and/or communication structures. The seeds may be configured to respond to the control device with a verification signal, indicating that the modified therapy program and communication structure have been implemented. Upon receiving the verification that the modified therapy program has been implemented (block 1216), the control device sends a signal to the first pacing seed to cause the first pacing seed to disable (block 1218). In embodiments, for example, the signal causes a deactivation element (e.g., as described herein with reference to FIGS. 1-7) to disable one or more components of the seed (e.g., a therapy circuit, a communications component, an oscillator, and/or the like). In embodiments, upon receiving the signal to disable therapy (block 1218) the first pacing seed sends an acknowledge signal back to the control device. After transmission of the acknowledge signal, the first pacing seed disables itself as described herein with reference to FIGS. 1-7.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

We claim:

1. An implantable medical device comprising:
   operational circuitry, wherein the operational circuitry comprises at least one of a therapy circuit and a sensor circuit;
   a communications module;
   a power source configured to deliver energy to the operational circuitry;
   a deactivation element configured to at least partially disable the operational circuitry by interrupting delivery of energy from the power source to the operational circuitry;
   a power manager configured to detect, based on a behavior of at least the communications module, an end-of-life condition of the power source and, in response to detecting the end-of-life condition, cause the deactivation element to at least partially reversibly disable the operational circuitry; and a controller configured to store, in a memory component and in response to the power manager detecting the end-of-life condition, an indication of an end-of-life state of the implantable medical device.

2. The implantable medical device of claim 1, wherein the implantable medical device comprises a leadless cardiac pacing seed.

3. The implantable medical device of claim 1, wherein the operational circuitry comprises the therapy circuit.

4. The implantable medical device of claim 3, wherein the deactivation element is configured to prevent energy from being delivered to the therapy circuit.

5. The implantable medical device of claim 1, wherein the memory component comprises an active storage element.

6. The implantable medical device of claim 5, wherein the power manager is configured to allow energy to be delivered to the memory component during the end-of-life state.

7. The implantable medical device of claim 1, wherein the memory component comprises a non-volatile memory element.

8. The implantable medical device of claim 7, wherein the memory component is further configured to store a plurality of operational parameters during the end-of-life state.

9. The implantable medical device of claim 8, wherein the power source comprises a rechargeable battery.

10. The implantable medical device of claim 9, wherein the controller is configured to access the plurality of operational parameters in response to receiving an activation signal.

11. The implantable medical device of claim 10, wherein the controller is configured to restore the device to its pre-end-of-life state using the operational parameters.

12. A leadless cardiac pacing seed comprising:
a therapy circuit;
a communications module;
a power source configured to deliver energy to the therapy circuit and the communications module;
a deactivation element configured to disable at least one of the therapy circuit and the communications module by reversibly interrupting delivery of energy from the power source to the therapy circuit or the communications module;
a power manager configured to detect, based on a behavior of at least the communications module, an end-of-life condition of the seed and, in response to detecting the end-of-life condition, cause the deactivation element to reversibly disable at least one of the therapy circuit and the communications module; and
a controller configured to store, in a memory component and in response to the power manager detecting the end-of-life condition, an indication of an end-of-life state of the implantable medical device.

13. The leadless cardiac pacing seed of claim 12, wherein the memory component comprises an active storage element.

14. The leadless cardiac pacing seed of claim 13, wherein the power manager is configured to allow energy to be delivered to the memory component during the end-of-life state.

15. The leadless cardiac pacing seed of claim 12, wherein the memory component comprises a non-volatile memory element.

16. The leadless cardiac pacing seed of claim 15, wherein the memory component is further configured to store a plurality of operational parameters during the end-of-life state, and wherein the controller is configured to access the plurality of operational parameters in response to receiving an activation signal.

17. The implantable medical device of claim 16, wherein the controller is configured to restore the device to its pre-end-of-life state using the operational parameters.

\* \* \* \* \*